(12) United States Patent
Flohr et al.

(10) Patent No.: US 7,924,970 B2
(45) Date of Patent: Apr. 12, 2011

(54) METHOD AND DEVICE FOR GENERATING A CT IMAGE WITH A HIGH TIME RESOLUTION

(75) Inventors: Thomas Flohr, Uehlfeld (DE); Rainer Raupach, Heroldsbach (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/695,256

(22) Filed: Jan. 28, 2010

(65) Prior Publication Data

US 2010/0195787 A1 Aug. 5, 2010

(30) Foreign Application Priority Data

Jan. 30, 2009 (DE) .......................... 10 2009 006 831

(51) Int. Cl.
*A61B 6/00* (2006.01)
(52) U.S. Cl. ........................ 378/5; 378/98.11; 378/98.12
(58) Field of Classification Search ........... 378/5, 98.11, 378/98.12
See application file for complete search history.

(56) References Cited

U.S. PATENT DOCUMENTS

| | | | | |
|---|---|---|---|---|
| 3,854,049 A * | 12/1974 | Mistretta et al. | ................ | 378/62 |
| 4,714,997 A * | 12/1987 | Crawford et al. | ............. | 600/425 |
| 6,845,142 B2 * | 1/2005 | Ohishi | .............................. | 378/8 |
| 7,379,575 B2 * | 5/2008 | Ruhrnschopf | ................ | 382/128 |
| 7,391,844 B2 * | 6/2008 | Wu et al. | .......................... | 378/18 |
| 2005/0163283 A1 | 7/2005 | Bruder et al. | | |

FOREIGN PATENT DOCUMENTS

DE 102004004295 A1 8/2005

* cited by examiner

*Primary Examiner* — Edward J Glick
*Assistant Examiner* — Alexander H Taningco
(74) *Attorney, Agent, or Firm* — Harness, Dickey & Pierce, P.L.C.

(57) ABSTRACT

A method and a device are disclosed for generating a CT image with a high time resolution using a computed tomography scanner which has at least two recording systems which are operated at different X-ray energy spectra. In at least one embodiment of the process, CT images are firstly reconstructed in each case from a semi-rotation with the two recording systems, with irradiated lengths of the contrast agent-enriched structures and the soft tissue being calculated therefrom. Subsequently, a common X-ray energy is assumed and artificial measurement data records are calculated therefor, using the knowledge of the irradiated lengths for both recording systems at the same common X-ray energy. The artificial measurement data of respectively a quarter-rotation per recording system is then used to calculate the final CT image with a high time resolution. The method affords the use of dual-energy scans without losing the high time resolution available in dual-source systems.

13 Claims, 3 Drawing Sheets

METHOD AND DEVICE FOR GENERATING A CT IMAGE WITH A HIGH TIME RESOLUTION

PRIORITY STATEMENT

The present application hereby claims priority under 35 U.S.C. §119 on German patent application No. DE 10 2009 006 831.7 filed Jan. 30, 2009, the entire contents of which are hereby incorporated herein by reference.

FIELD

At least one embodiment of the present invention generally relates to a method and/or a device for generating a CT (computed tomography) image of an object. For example, it may relate to one which has contrast agent-enriched structures and soft tissue, using a computed tomography scanner which has at least n=2 recording systems which are arranged on a rotating frame, angularly offset by an angle of 180°/n with respect to one another and which are operated at different X-ray energies.

BACKGROUND

In the case of two recording systems, such computed tomography scanners are also known as dual-source CT systems. Here, a recording system is understood to mean the combination of an X-ray source and an opposing X-ray detector. Dual-source CT systems are used, inter alia, for cardiac recordings. In order to optimize the time resolution in EKG-synchronized cardiac recordings, data from a quarter-rotation (in parallel geometry) of the rotating frame is used per recording system for generating a CT image. Compared to CT systems with only one recording system, the time resolution is doubled as a result of this. In the vicinity of the center of the rotation, the time resolution using a dual-source CT system is a quarter of the rotational time of the rotating frame. However, the image reconstruction from the measurement data of the two recording systems assumes that both systems are operated at the same X-ray energy spectrum in order to obtain an artifact-free image.

If the two recording systems are operated at different X-ray energies or X-ray energy spectra, as is the case in EKG-synchronized dual-energy recordings, two quarter-rotation data records cannot simply be combined to generate an image since the data is inconsistent as a result of the different X-ray energy spectra, and the different mean X-ray energies resulting from this. The result of this inconsistency is artifacts and CT value displacements in CT images where the semi-rotation for acquiring the measurement data, as a minimum requirement for image reconstruction, is composed of a quarter-rotation per recording system. Therefore, EKG-synchronized dual-energy recordings using a dual-source CT system previously utilized measurement data of a semi-rotation per recording system which suffice for generating a separate image per recording system. The two separate images were then suitably combined to form a mixed image. However, as a result of this, the time resolution is only half of the rotational time of the rotating frame and so the actual advantage of using dual-source CT systems, namely the generation of EKG-synchronized images with optimized time resolution of a quarter of the rotational time, is lost.

The subsequently published document DE 10 2008 051 043, the entire contents of which are hereby incorporated herein by reference, describes a method for optimizing the time resolution in EKG-synchronized dual-energy dual-source CT recordings. Herein, the inconsistent measurement data of the two recording systems recorded at different X-ray spectra are decomposed into a spatial low-frequency component and a spatial high-frequency component. The frequency boundary is selected such that relevant movements of the coronary arteries are substantially contained in the spatial high-frequency component of the data and, by contrast, the inconsistencies produced by the different mean energy of the measurement data are substantially contained in the spatial low-frequency component. The low-frequency data generates an image with at least one semi-rotation per recording system, whereas only a quarter-rotation per recording system is used for the diagnostically relevant high-frequency measurement data in order to optimize the time resolution. However, the time resolution of the image in this method is dependent on the spatial frequency of the imaged structures and a clean separation between spatial high-frequency moved structures, especially coronary arteries, and low-frequency artifacts is not always ensured.

SUMMARY

In at least one embodiment of the present invention, a method and a device are specified for generating CT images with a high time resolution using a computed tomography scanner which has at least two recording systems which are operated at different X-ray energies, wherein the CT images should have as few artifacts as possible.

In at least one embodiment of the proposed method, use is made of a computed tomography scanner which has at least n=2 recording systems which are arranged on a rotating frame of the computed tomography scanner, angularly offset by an angle of 180°/n with respect to one another and which are operated at different X-ray energy spectra and hence at different mean X-ray energies. In the case of a computed tomography scanner with n=2 recording systems; this corresponds to the known dual-source CT systems.

However, at least one embodiment of the method can also be performed by CT systems which have more than two recording systems which are arranged on the rotating frame angularly offset with respect to one another as described above. Here, the individual recording systems are composed in a known fashion from an X-ray source, especially an X-ray tube, and an opposing X-ray detector. The different mean X-ray energies or X-ray energy spectra can be produced, for example, by applying different tube voltages, e.g. of 80 kV and 140 kV, to the two X-ray tubes. This subsequently leads to different mean X-ray energies per recording system.

Within the scope of at least one embodiment of the method, measurement data of the object at the different X-ray energy spectra is recorded by the recording systems during a semi-rotation of the rotating frame and respectively one preliminary CT image of the object is reconstructed from the measurement data for each of the recording systems. In this case, a semi-rotation is understood to be a CT scan over 180° plus the fan angle of the X-ray beam bundle, and a quarter-rotation is understood to be a CT scan over 90° plus fan angle, and possibly plus transition angle. The contrast agent-enriched structures are then segmented in the preliminary CT images in order to respectively obtain a contrast agent image and a soft tissue image. The contrast agent and soft tissue images are subjected to a re-projection and so contrast agent projection data and soft tissue projection data are obtained. A person skilled in the art knows the technique of re-projection. In the process, beams are placed through the CT image (volume image) in the respective projection direction and the gray-scale values or CT values of the pixels situated on the respective beams are summed in order to obtain the projection data of the respective projection or projection direction.

Using the projection data obtained thus and the known mean absorption coefficients of the utilized contrast agent and the soft tissue at the different X-ray energies, the respectively irradiated lengths of the contrast agent-enriched structures and of the soft tissue are calculated for each projection. These calculated irradiated lengths for each projection are then used to calculate for each recording system an artificial measurement data record for an angular range of 180°/n, for a common X-ray energy or a common X-ray energy spectrum which can be selected by the user, with the angular ranges complementing one another to form a semi-rotation. The CT image is then reconstructed from the artificial measurement data records of the recording systems, which now have the same common X-ray energy or the same common X-ray energy spectrum. In the case of two recording systems, this reconstruction corresponds to the procedure utilized in dual-source CT systems with the same X-ray energy spectra of the two recording systems for optimizing the time resolution. Here, the common X-ray energy is preferably selected between the mean X-ray energies of the recoding systems and can, for example, be the mean value of the mean X-ray energies of the X-ray energy spectra of the recording systems.

The mean absorption coefficients of the contrast agent and soft tissue at the different X-ray energy spectra or mean X-ray energies required for calculating the irradiated lengths and for generating the artificial measurement data records can, for example, be combined in advance in a spreadsheet which is subsequently accessed within the scope of at least one embodiment of the method.

As a result of the proposed procedure, a time resolution of a quarter-rotation is achieved in the case of n=2 recording systems, as is known in dual-source CT systems with equal X-ray energy spectra. However, the advantage of the dual-energy recordings can be utilized at the same time in order to obtain, for example, additional information in respect of the composition of the examination object.

The segmentation of the contrast agent-enriched structures can be performed in a known fashion, for example using a thresholding method in which all pixels in the CT image with a grayscale value below or above a predetermined threshold are assigned to the structure, and all remaining pixels are assigned to the soft tissue. A person skilled in the art knows of such segmentation techniques.

At least one embodiment of the proposed method is particularly suitable for cardiac examinations, for example for the EKG-synchronized recording of the heart. In the process, the method allows the calculation of, for example, EKG-synchronized dual-energy dual-source CT images with an optimized time resolution of a quarter of the rotational time of the rotating frame. Here, the time resolution does not depend on the spatial frequency of the imaged structures. Nor is an arbitrary and possibly problematic separation of spatial low-frequency artifacts and spatial high-frequency relevant image structures necessary.

A suitable device for performing at least one embodiment of the method comprises an X-ray CT system with at least two recording systems, respectively comprising an X-ray source and an X-ray detector, which are arranged angularly offset by an angle of 180°/n with respect to one another on the rotating frame of the CT system. A reconstruction module is provided in a control and computational unit which is part of the CT system and it generates the final CT image with a high time resolution from the measurement data of the recording systems as per the proposed method and via the corresponding intermediate steps.

BRIEF DESCRIPTION OF THE DRAWINGS

In the following text, the proposed method will once again be described in more detail on the basis of the attached drawings, in which.

DETAILED DESCRIPTION OF THE EXAMPLE EMBODIMENTS

Figure 1:
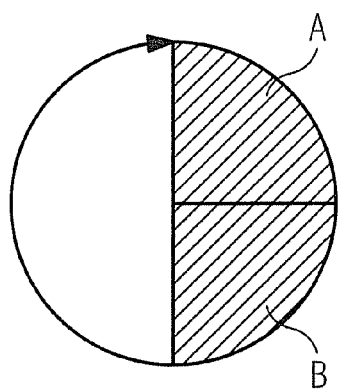
FIG. 1 shows a schematic illustration of the utilized angular ranges in a dual-source CT reconstruction over 2×90°.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes,"

and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 schematically shows the utilized angular ranges in a CT scan using a dual-source CT system for obtaining an optimized time resolution. In this case, the two recording systems are arranged on the rotating frame, angularly offset by 90° with respect to one another, and so, in total, measurement data over an angular range of 180° is recorded during a quarter-rotation of the rotating frame. Here, each of the two recording systems A and B acquires an angular range of 90°. Thus, the combined measurement data allows the reconstruction of a CT image with a time resolution of a quarter of the rotation time of the rotating frame.

However, if the two recording systems are operated at different X-ray energy spectra, the contrast information present in the raw or measurement data of the two systems differs in the different spectra and so image artifacts are created during an image reconstruction. Previously, this led to measurement data not of a quarter-rotation but of a semi-rotation having to be used for the reconstruction of each CT image and so the time resolution was correspondingly lower.

Figure 2:
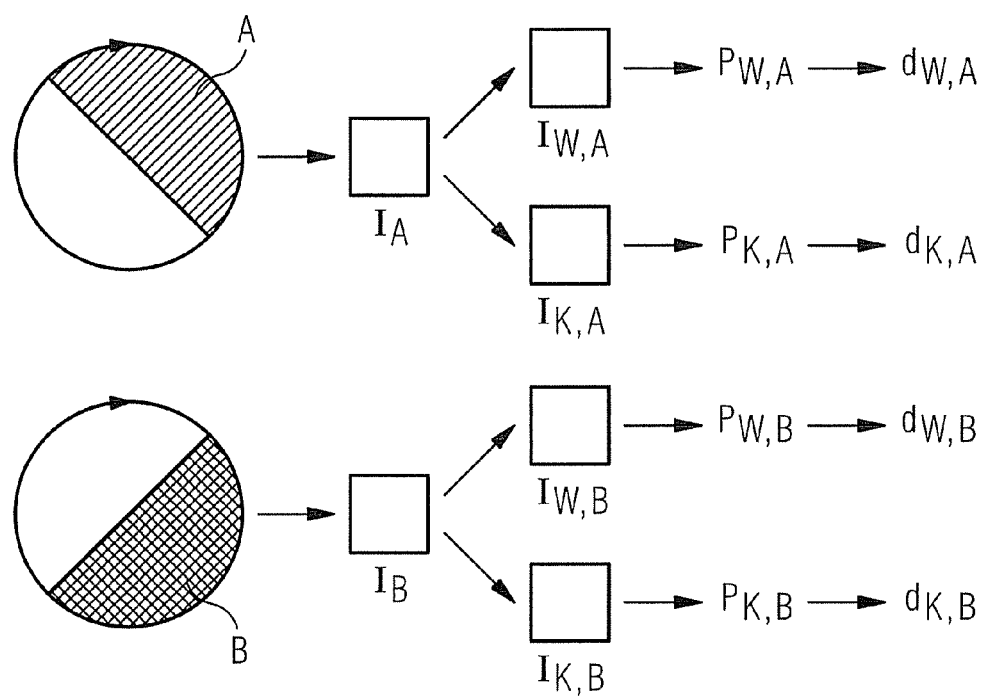
FIG. 2 shows a schematic illustration of a first step of the proposed method with an illustration of the utilized angular ranges during the recording.

Although in an embodiment of the proposed method a semi-rotation per CT image is now likewise performed, the final CT image is reconstructed on the basis of artificially generated measurement data of a quarter-rotation and thus has an increased time resolution. This example likewise assumes a dual-source CT system with two recording systems which are arranged on the rotating frame, angularly offset by 90° with respect to one another. Both recording systems are operated at a different tube voltage and hence at a different mean energy of the X-ray spectrum. First of all, there is a recording using both recording systems over a semi-rotation of the rotating frame. The two angular ranges for the recording systems A and B covered thereby are indicated in FIG. 2.

The measurement data from the two recording systems A and B from this at least one semi-rotation is used to calculate a complete image $I_A$ and $I_B$ per recording system. In the case of cardiac recordings, essential structures in this image are the soft tissue and the vessels and chambers of the heart filled with contrast agent, which can easily be separated in the image by a threshold. As a result of a segmentation based thereon, a soft tissue image $I_{W,A}$ and $I_{W,B}$ and a contrast agent image $I_{K,A}$ and $I_{K,B}$ are obtained per recording system. The different X-ray absorption of the contrast agent-filled structures in the contrast agent images $I_{K,A}$ and $I_{K,B}$ at different mean X-ray energies is the main reason for the above-described data inconsistencies.

In the next step, soft tissue projections $P_W$ and contrast agent projections $P_K$ are generated for the respective angular range of each recording system by re-projection from the soft tissue images $I_{W,A}$ and $I_{W,B}$ and the contrast agent images $I_{K,A}$ and $I_{K,B}$. This is likewise indicated in FIG. 2. The soft tissue and contrast agent projections of recording system A have the mean energy $E_A$; the soft tissue and contrast agent projections of recording system B have the mean X-ray energy $E_B$. Using the known mean absorption coefficients of soft tissue and contrast agent—generally iodine—at the energies $E_A$ and $E_B$, the irradiated lengths $d_{W,A}$ and $_{W,B}$ of soft tissue and $d_{K,A}$ and $d_{K,B}$ of contrast agent can be calculated for each projection.

Now, a common mean energy $E_M$, advantageously between $E_A$ and $E_B$, is assumed for both measurement systems. Using the known absorption coefficients of soft tissue and contrast agent at $E_M$, new overall projections P' at the same mean energy $E_M$ can be generated per recording system with knowledge of $d_{W,A}$ and $d_{W,B}$ and $d_{K,A}$ and $d_{K,B}$. These calculations are respectively performed in a known fashion using the absorption law.

Figure 3:
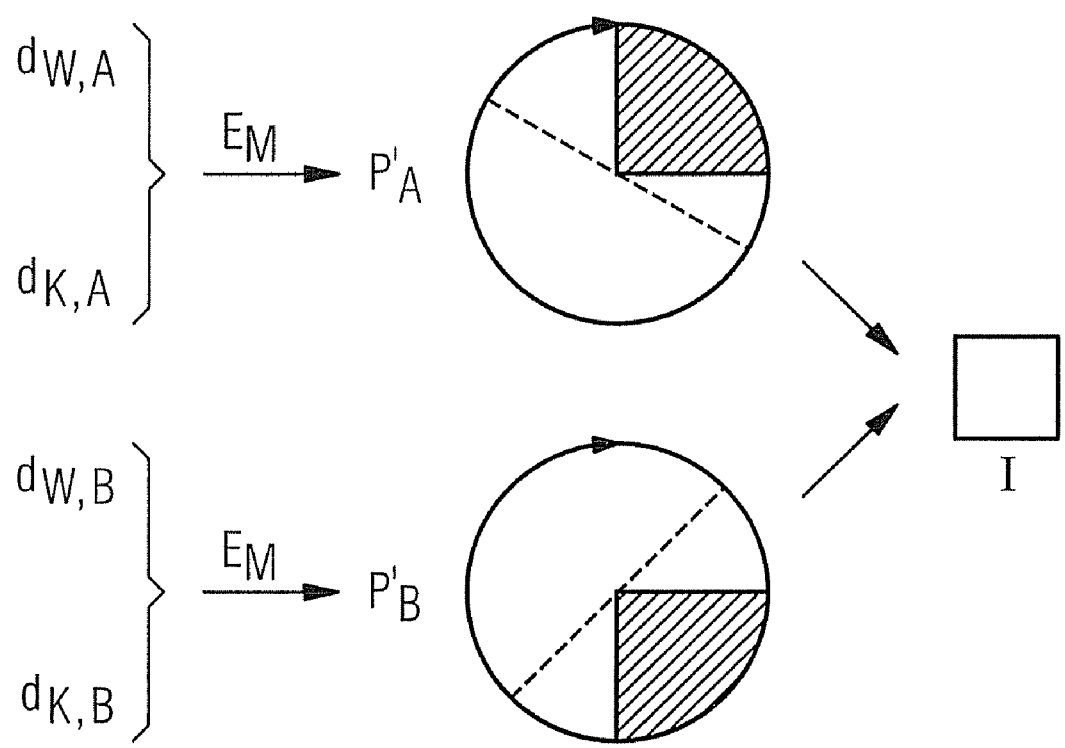
FIG. 3 shows a schematic illustration of further method steps of the proposed method for generating artificial measurement data records.

Thus, artificial measurement data is available for each of the two recording systems A and B at the X-ray energy $E_M$, i.e. at the same X-ray energy for both recording systems. Now, a CT image with an optimized time resolution can be calculated from this artificial measurement data using respectively a quarter-rotation per recording system. This is once again illustrated on the basis of FIG. 3, which indicates the angular ranges of the artificial measurement data of the two recording systems from which the final CT image I is calculated.

Figure 4:
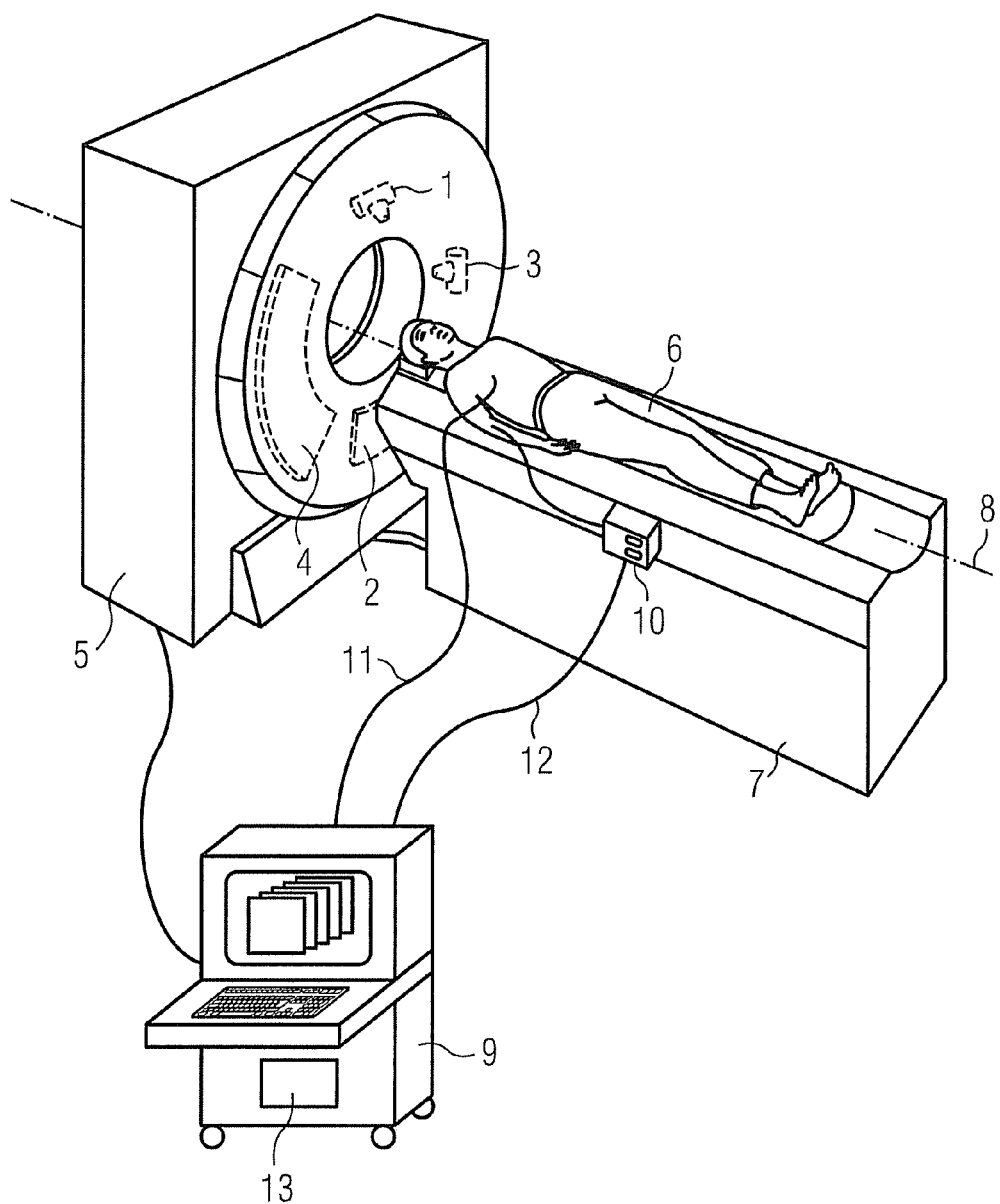
FIG. 4 shows an X-ray CT system for generating dual-energy scans and a CT image as per an embodiment of the proposed method.

Finally, FIG. 4 shows an X-ray CT system which is designed for carrying out the proposed method. A dual-energy CT system with a housing 5 for the rotating frame is illustrated in this figure in an exemplary fashion. A first recording system in the form of an X-ray tube 1 with an opposing first detector 2 is attached to the rotating frame for the scan at a first X-ray energy spectrum. Additionally, a second recording system with a second X-ray tube 3 with an opposing second detector 4 is arranged on the rotating frame, as a result of which a scan can be carried out at a different X-ray energy spectrum. Thus, this system permits a simultaneous scan at two different X-ray energy spectra using the two recording systems arranged offset by an angle of 90°.

A patient 6 is situated on a patient couch 7 which can be displaced in the direction of the system axis 8 and by means of which the patient can, during a scan, be pushed, continuously or sequentially, along the system axis 8 and through a measurement field between the X-ray tubes and the respectively assigned detectors. Should the detector have a sufficient width for a provided examination field, it is also possible for the patient with this examination field, e.g. the cardiac region, to be displaced into the measurement region of the detector and for circular scans to be performed there on a stationary patient, i.e. without a further displacement of the patient. This type of scan, which does not require a sequential or continuous feed, can be used particularly advantageously for perfusion measurements in the context of the method according to the invention. In the process, a contrast agent applicator 10, connected to the control and computational unit 9 via a control line 12, can be used to apply contrast agent to the patient before or during the scanning procedure. Observation of this contrast agent in the cardiac region allows the perfusion of the contrast agent to be observed in a known fashion and medically relevant perfusion parameters can be determined in a known fashion.

The scanning procedures are controlled by the control and computational unit 9 with the aid of computer programs. Additionally, cardiac potentials of the patient 6 can be recorded during the scanning procedure with the aid of an EKG line 11 and so information correlated with respect to time between the recorded CT data records and the cardiac motion can be stored. The computational and control unit 9 can likewise perform the reconstruction. According to an embodiment of the invention, the computational and control unit 9 also has a module 13 for generating a CT image via the intermediate steps of an embodiment of the proposed method.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating a CT image of an object, the object including contrast agent-enriched structures and soft tissue, using a computed tomography scanner which includes at least $n=2$ recording systems which are arranged on a rotating frame of the computed tomography scanner, angularly offset by an angle of $180°/n$ with respect to one another and which are operated at different X-ray energy spectra, the method comprising:

recording measurement data of the object at the different X-ray energy spectra during a semi-rotation of the rotating frame with the recording systems;

respectively reconstructing a preliminary CT image of the object from the measurement data for each of the respective recording systems;

segmenting the contrast agent-enriched structures in the preliminary CT images in order to respectively obtain a contrast agent image and a soft tissue image;

subjecting the contrast agent and soft tissue images to a re-projection in order to obtain contrast agent projection data and soft tissue projection data;

calculating irradiated lengths of the structures and the soft tissue for each projection from the projection data and known mean absorption coefficients of the contrast agent and the soft tissue at the different X-ray energy spectra;

calculating an artificial measurement data record for an angular range of $180°/n$ for each recording system on the basis of the calculated irradiated lengths for a common X-ray energy or a common X-ray energy spectrum, with the angular ranges complementing one another to form a semi-rotation; and reconstructing the CT image from the artificial measurement data records.

2. The method as claimed in claim 1, wherein a mean value is selected from the mean X-ray energies of the different X-ray energy spectra of the recording systems as common X-ray energy.

3. The method as claimed in claim 2, wherein the segmentation is performed using a thresholding method.

4. The method as claimed in claim 3, wherein the measurement data is recorded under EKG control.

5. The method as claimed in claim 4, wherein the different X-ray energy spectra are produced by operating the X-ray tubes of the recording systems at different tube voltages.

6. The method as claimed in claim 2, wherein the measurement data is recorded under EKG control.

7. The method as claimed in claim 2, wherein the different X-ray energy spectra are produced by operating the X-ray tubes of the recording systems at different tube voltages.

8. The method as claimed in claim 1, wherein the segmentation is performed using a thresholding method.

9. The method as claimed in claim 1, wherein the measurement data is recorded under EKG control.

10. The method as claimed in claim 1, wherein the different X-ray energy spectra are produced by operating the X-ray tubes of the recording systems at different tube voltages.

11. A computed tomography scanner for generating a CT image of an object, comprising:

at least n=2 recording systems, arranged on a rotating frame and angularly offset by an angle of 180°/n with respect to one another, the at least n=2 recording systems being operable at different X-ray energy spectra; and a control and computational unit, in which a reconstruction module is formed to generate a CT image with a high time resolution from the measurement data of the recording systems as per the method as claimed in claim 1.

12. A non-transitory computer readable medium including program segments for, when executed on a computer device, causing the computer device to implement the method of claim 1.

13. A computed tomography scanner for generating a CT image of an object, comprising:

at least n=2 recording systems, arranged on a rotating frame and angularly offset by an angle of 180°/n with respect to one another, the at least n=2 recording systems being operable at different X-ray energy spectra to record measurement data of the object at the different X-ray energy spectra during a semi-rotation of the rotating frame with the recording systems; and a control and computational unit, in which a reconstruction module is formed to generate a CT image the measurement data of the recording systems by:

respectively reconstructing a preliminary CT image of the object from the measurement data for each of the respective recording systems, segmenting the contrast agent-enriched structures in the preliminary CT images in order to respectively obtain a contrast agent image and a soft tissue image, subjecting the contrast agent and soft tissue images to a re-projection in order to obtain contrast agent projection data and soft tissue projection data, calculating irradiated lengths of the structures and the soft tissue for each projection from the projection data and known mean absorption coefficients of the contrast agent and the soft tissue at the different X-ray energy spectra, calculating an artificial measurement data record for an angular range of 180°/n for each recording system on the basis of the calculated irradiated lengths for a common X-ray energy or a common X-ray energy spectrum, with the angular ranges complementing one another to form a semi-rotation, and reconstructing the CT image from the artificial measurement data records.

* * * * *